United States Patent [19]

Panzani et al.

[11] Patent Number: 5,039,482
[45] Date of Patent: Aug. 13, 1991

[54] INTEGRATED UNIT FOR EXTRACORPOREAL BLOOD CIRCUITS

[75] Inventors: Ivo Panzani, Mirandola; Nicola Ghelli, San Pietro in Casale; Pietro Vescovini, Medolla, all of Italy

[73] Assignee: Shiley Inc., Irvine, Calif.

[21] Appl. No.: 282,152

[22] Filed: Dec. 9, 1988

[30] Foreign Application Priority Data

Dec. 15, 1987 [IT] Italy .................. 23011 A/87

[51] Int. Cl.$^5$ ............................................. A61M 1/14
[52] U.S. Cl. ........................................ 422/46; 422/47; 422/48; 128/DIG. 3; 261/DIG. 28; 55/16; 55/158
[58] Field of Search ............... 422/46, 47, 48; 128/DIG. 3; 261/DIG. 28; 55/16, 158

[56] References Cited

U.S. PATENT DOCUMENTS

| | | | |
|---|---|---|---|
| 4,073,622 | 2/1978 | Luppi | 422/47 |
| 4,182,739 | 1/1980 | Curtis | 422/47 |
| 4,451,562 | 5/1984 | Elgas et al. | 422/46 X |
| 4,585,056 | 4/1986 | Oscarsson | 422/46 X |
| 4,698,207 | 10/1987 | Bringham et al. | 422/46 |
| 4,818,490 | 4/1989 | Carson et al. | 422/46 |

Primary Examiner—Robert J. Warden
Assistant Examiner—Lynn M. Kummert
Attorney, Agent, or Firm—Peter C. Richardson; Larry C. Akers; Roger C. Turner

[57] ABSTRACT

An extracorporeal blood circuit comprises a generally cylindrically shaped blood reservoir; a generally cylindrically shaped oxygenator arranged coaxially and adjacently below said reservoir; and a generally cylindrically shaped heat exchanger attached coaxially and adjacently below said oxygenator. The reservoir encloses an upper defoamer and multiple filter element adapted to receive cardiotomy blood within the interior of said upper element and to discharge treated blood to said reservoir; and a lower defoamer and filter element adapted to receive arterial blood within the interior of said lower element and to discharge treated blood to said reservoir; and has a lower blood outlet. The oxygenator has an inlet adapted to integrally receive blood directly from the outlet of said heat exchanger and an outlet adapted to return the oxygenated blood to the patient.

5 Claims, 1 Drawing Sheet

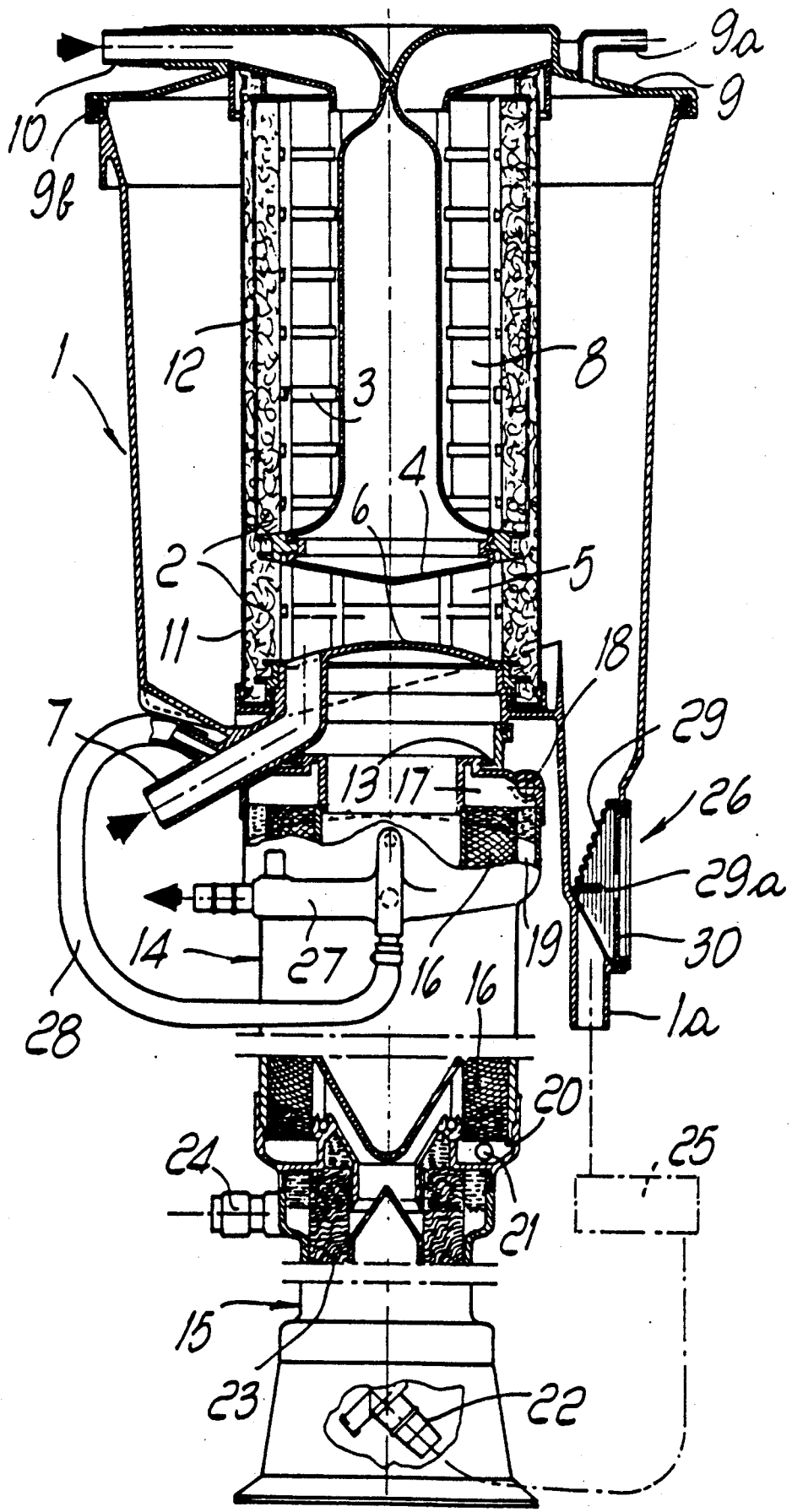

INTEGRATED UNIT FOR EXTRACORPOREAL BLOOD CIRCUITS

BACKGROUND OF THE INVENTION

The invention relates to an integrated unit for extracorporeal blood circuits.

It is generally known that during some surgical operations it is necessary to provide extracorporeal blood circulation in a circuit which comprises a plurality of known devices connected by means of connecting lines. One such device is the venous reservoir which collects blood coming from the patient, and another device is the cardiotomy reservoir which acts as blood storage container and which normally receives recovery blood from the operating field. In extracorporeal circulation, blood must sometimes give off or receive heat, and thus a heat exchanger is provided in which blood, passing through it exchanges heat with a fluid (normally water); and it is also necessary to oxygenate the blood, and thus an oxygenator is provided.

In known extracorporeal circuits, each of these devices may be independent from one another and separately mounted and interconnected with numerous connecting lines, or in some systems they may be at least partially integrated. The separate multiple devices leads to difficulties in installation due to the complication of the required connections and to the difficulties in the placement of all the devices within a limited space proximate to the operating field. In addition, various sensors and electrical warning devices are required to indicate when a dangerously low level of blood is present in the reservoir so that air is not delivered into the patient.

An object of the present invention is to provide an integrated unit for extracorporeal blood circuits which is compact, efficient, and easy to install and operate, and which provides grater safety for the patient.

SUMMARY OF THE INVENTION

The proposed object is achieved by an integrated unit for an extracorporeal blood circuit comprising a generally cylindrically shaped blood reservoir; a generally cylindrically shaped oxygenator arranged coaxially and adjacently below said reservoir; and a generally cylindrically shaped heat exchanger attached coaxially and adjacently below said oxygenator. The reservoir encloses a generally cylindrically shaped upper defoamer and multiple filter element adapted to receive cardiotomy blood within the interior of said upper element and to discharge treated blood to said reservoir; and a lower defoamer and filter element adapted to receive arterial blood within the interior of said lower element and to discharge treated blood to said reservoir, and the reservoir has a lower blood outlet. "The lower end of the reservoir is readily attachable and detachable with the upper end of oxygenator." The heat exchanger has a blood a blood outlet and is adapted to circulate blood around a heat exchange element. The oxygenator includes a plurality of microporous membrane fibers and is adapted to circulate oxygen within the fibers and to circulate blood around the fiber and has an inlet adapted to integrally receive blood directly from the outlet of said heat exchanger and an outlet adapted to return the oxygenated blood to the patient. The unit is adapted to have a pump interconnected between the outlet of said reservoir and the blood inlet of said heat exchanger to pump blood through the unit. "The unit includes a mechanical safety device at the reservoir blood outlet to occlude the outlet at a predetermined low level of blood to prevent the possibility of air being returned to the blood of the patient."

BRIEF DESCRIPTION OF THE DRAWINGS

While the novel feature of the invention are set forth with particularity in the appended claims, the invention will be better understood along with other features thereof from the following detailed description taken in conjunction with the drawing, in which, FIG. 1, a front elevational view in section illustrating the structure and function of the integrated unit.

DESCRIPTION OF THE PREFERRED EMBODIMENT

Referring to FIG. 1, the reservoir 1 encloses a defoaming material 2 and filter elements supported by structure 3, arranged in the shape of a central volume displacement core and a spaced cylindrical wall which defines an interior space which is divided by a lateral partition 4 into a lower compartment 5 and an upper compartment 8. The reservoir includes an arterial inlet 7 to receive blood coming from a patient within the lower compartment 5 which is further defined by a lower partition 6. The reservoir has a top cover 9 including a cardiotomy inlet 10 to receive blood coming from the operating field into the upper compartment 8. The top cover is preferably rotatably attached to the reservoir so that inlet 10 can be independently oriented as desired to facilitate connection to the operating field. The reservoir encloses the lower defoamer 2 and filter element 11 and an upper defoamer and multiple filter element 12. The filter elements could be separate and distinct but are preferably combined into an integrally cylindrically stacked arrangement as illustrated. The filter element 11 is typically a porous screen which completely surrounds the defoaming material 2 and is sufficient for treating the arterial blood coming from the patient. The cardiotomy blood coming from the operating field requires the filter 12 which typically includes a defoamer 2, filter 11, and an additional defoamer and depth filter (felt) material to treat the cardiotomy blood. After passing through the defoaming material and being appropriately filtered, the treated arterial blood and cardiotomy blood is collected within the cylindrical interior defined by the wall of the reservoir 1.

The lower end of reservoir 1 is attachably and detachably connected by a known quick connection 13 to the upper end of the oxygenator 14 which is integrally attached and internally connected to the heat exchanger 15, to complete a compact integral unit.

The oxygenator 14 is preferably highly efficient and includes a bundle of membrane fibers 16 embedded at the ends into rings of polyurethane resin, termed "potting"; the housing (14) and the upper potting determines an annular oxygen compartment 17 having a duct 18 for the inflow of oxygen and an upper annular blood compartment 19, while the lower potting determines an oxygen compartment 20 having a duct 21 for the outflow thereof.

The heat exchanger 15, includes an inlet and outlet illustrated as 24, and has a flow path for the temperature controlled fluid. It further includes a blood inlet 22 (from the reservoir) and a separate flow path over common heat exchange surfaces 23 which are typically formed of radially pleated metallic (stainless steel) surfaces.

In operation, the blood is drawn, under the action of a pump 25, from the reservoir 1 by means of the connection 1a controlled by a mechanical safety device indicated by 26 (Which will be described in detail hereinafter) and is sent to the inlet 22 of the heat exchanger 15, after passing therethrough it exits directly into the lower end of the oxygenator 14, and circulates around the exterior of the capillaries of the bundle 16 and into the compartment 19 to exit by means of a duct 27 to return the treated oxygenated blood to the patient.

A bypass line 28 is provided which directly connects the outlet duct 27 from the oxygenator 14 to the venous inlet 7 of the reservoir. The bypass line can be opened or closed by a clamp or valve (to bypass the patient) to permit recirculation of blood from the oxygenator back to the reservoir. Although the bypass line is normally closed, it facilitates the initial priming of the unit, allows for additional oxygenation of the blood when deemed necessary and permits circulation of blood within the unit whenever it is desired.

In normal operation, the reservoir 1 contains blood at atmospheric pressure, which is vented to the atmosphere by means of a connector 9a. The reservoir must never empty during operation since the pump 25 could then aspirate air into the patient, which would be extremely harmful. This is usually monitored by secondary control means such as electronic sensors which activate alarms and cut-off switches. The present invention includes the aforementioned safety device 26 which directly and automatically prevents the pump from drawing air from the reservoir. The safety device comprises an elastic membrane 29 fixed within a housing having a cover 30 and which has a surface adapted to occlude the outlet 1a. The membrane is normally in the closed occluded position and is calibrated to actuate into the open non-occluded position only by a minimum predetermined hydrostatic pressure provided by a sufficient quantity of blood which must be present in the reservoir. It is readily seen that such a mechanical safety device would reliably and directly prevent air from being withdrawn by the pump when the hydrostatic load reaches a value corresponding to the minimum level of blood in the tank. A suitable safety valve is formed from a thin, flexible silicone membrane having a flat sealing surface surrounded by concentric circular (or oval shaped) convolutions. A grip tab 29a is provided which permits the surgeon to manually actuate the membrane.

The mechanical safety device 26; is preferably integrated within the structure of the reservoir 1, however, it can also be provided as a separate autonomous device. In such a separate device, the elastic membrane 29 and the cover 30 are associated with an enclosed structure adapted to be connected to the reservoir at 1a between the reservoir 1 and the pump 25.

As previously discussed, the integrated unit permits the reservoir to be readily detached from the oxygenator-heat exchanger, which allows its further use in post operative care. One such use is in the post operative recovery of blood from drainages. In this use, a negative pressure (vacuum line) is attached to connection 9a. The reservoir includes a typical sealing gasket 9b around the rotatable top 9 to facilitate a seal for this use.

The advantages of the present invention are apparent in the compact versatile structure along with the reduction of connecting lines to facilitate installation and operation of the unit. The additional, direct and reliable safety device is also a significant feature of the unit.

The described invention is susceptible to numerous modifications and variations, all of which are considered to be within the scope of the inventive concept as defined by the following claims.

We claim:

1. An integrated unit for an extracorporeal blood circuit comprising:
   a generally cylindrically shaped blood reservoir having an upper cardiotomy blood inlet, a lower arterial blood inlet, and a lower blood outlet;
   a generally cylindrically shaped oxygenator arranged coaxially and adjacently below said reservoir;
   and a generally cylindrically shaped heat exchanger having a blood inlet, a blood outlet and a flow path around a heat exchange element, and attached coaxially and adjacently below said oxygenator;
   wherein said reservoir encloses a generally cylindrically shaped upper defoamer and multiple filter element for receiving cardiotomy blood from said cardiotomy blood inlet within the interior of said upper defoamer and multiple filter element and for discharging treated blood within said reservoir; and a lower defoamer and filter element for receiving arterial blood from said arterial blood inlet within the interior of said lower element and for discharging treated blood within said reservoir; and having the lower reservoir blood outlet for interconnection with said blood inlet of said heat exchanger;
   said oxygenator including a plurality of microporous membrane fibers for circulating oxygen within the fibers and a flow path including an inlet for receiving blood from the outlet of said heat exchanger and circulating the blood around the fibers for oxygenating the blood, and having an outlet for returning the oxygenated blood to the patient; and
   an elastic membrane positioned within said reservoir adjacent the blood outlet thereof whereby the device is normally in the closed occluded position and is retained in the open non-occluded position only by a minimum predetermined hydrostatic pressure corresponding to a sufficient quantity of blood present in the reservoir.

2. The unit as in claim 1 wherein said elastic membrane comprises a series of concentric generally circular convolutions having an occluding portion conforming to the shape of the reservoir blood outlet.

3. A safety device for a blood reservoir for use in an extracorporeal blood circuit in which the reservoir includes an inlet and a lower blood outlet for interconnection with a heat exchanger and an oxygenator, comprising:
   an elastic membrane positioned adjacently to the blood outlet which occludes the outlet of the reservoir at a predetermined low level of blood to prevent the possibility of air being discharged from the reservoir outlet.

4. The device as in claim 3 wherein said elastic membrane comprises a series of concentric generally circular convolutions having an occluding portion conforming to the shape of the reservoir blood outlet.

5. An integrated unit for an extracorporeal blood circuit comprising:
   a generally cylindrically shaped blood reservoir having an upper cardiotomy blood inlet, a lower arterial blood inlet, and a lower blood outlet;
   a generally cylindrically shaped oxygenator arranged coaxially and adjacently below said reservoir;

and a generally cylindrically shaped heat exchanger having a blood inlet, a blood outlet and a flow path around a heat exchange element, and attached coaxially and adjacently below said oxygenator;

wherein said reservoir encloses a generally cylindrically shaped upper defoamer and multiple filter element for receiving cardiotomy blood from said cardiotomy blood inlet within the interior of said upper defoamer and multiple filter element and for discharging treated blood within said reservoir; and a lower defoamer and filter element for receiving arterial blood from said arterial blood inlet within the interior of said lower element and for discharging treated blood within said reservoir; and having the lower reservoir blood outlet for interconnection with said blood inlet of said heat exchanger;

said oxygenator including a plurality of microporous membrane fibers for circulating oxygen within the fibers and a flow path including an inlet for receiving blood from the outlet of said heat exchanger and circulating the blood around the fibers for oxygenating the blood, and having an outlet for returning the oxygenated blood to the patient; and a mechanical safety device means at the reservoir blood outlet wherein said safety device means occludes the outlet of said reservoir at a predetermined low level of blood to prevent the possibility of air being discharged from the reservoir outlet, wherein said safety device means is not integral with said reservoir but is a separate component comprising a housing having an inlet interconnected to the outlet of said reservoir, a device outlet, and an elastic membrane which is normally closed occluding said device outlet and which is retained in the open non-occluded position by a force corresponding to a minimum hydrostatic pressure corresponding to a quantity of blood present in the reservoir and above the membrane.

* * * * *